US012678563B2

(12) United States Patent
Wine

(10) Patent No.: US 12,678,563 B2
(45) Date of Patent: Jul. 14, 2026

(54) UNIVERSAL FLOW LIMITER ASSEMBLY

(71) Applicant: CAREFUSION 303, INC., San Diego, CA (US)

(72) Inventor: Jason Andrew Wine, Placentia, CA (US)

(73) Assignee: CAREFUSION 303, INC., San Diego, CA (US)

( * ) Notice: Subject to any disclaimer, the term of this patent is extended or adjusted under 35 U.S.C. 154(b) by 890 days.

(21) Appl. No.: 17/982,482

(22) Filed: Nov. 7, 2022

(65) Prior Publication Data

US 2023/0191025 A1 Jun. 22, 2023

Related U.S. Application Data

(60) Provisional application No. 63/292,306, filed on Dec. 21, 2021.

(51) Int. Cl.
*A61M 5/168* (2006.01)
(52) U.S. Cl.
CPC .... *A61M 5/16877* (2013.01); *A61M 5/16813* (2013.01)
(58) Field of Classification Search
CPC .......... A61M 5/16877; A61M 5/16813; A61M 39/284; A61M 39/285; A61M 39/287; A61M 5/14; A61M 5/142; A61M 2205/3334; A61M 39/283; F16K 7/06; F16K 7/061; F16K 7/066
See application file for complete search history.

(56) References Cited

U.S. PATENT DOCUMENTS

| | | | | | |
|---|---|---|---|---|---|
| 3,497,175 | A | * | 2/1970 | Koland | A61M 39/286 |
| | | | | | 251/8 |
| 3,612,474 | A | | 10/1971 | Strohl, Jr. | |
| 4,091,815 | A | | 5/1978 | Larsen | |
| 4,585,442 | A | | 4/1986 | Mannes | |
| 4,620,690 | A | * | 11/1986 | Kamen | A61M 39/28 |
| | | | | | 251/8 |
| 2005/0020978 | A1 | | 1/2005 | Vollenweider | |
| 2011/0098661 | A1 | * | 4/2011 | Jedweb | A61M 39/284 |
| | | | | | 604/250 |

FOREIGN PATENT DOCUMENTS

| | | | | |
|---|---|---|---|---|
| EP | 0399736 A1 | 11/1990 | | |
| GB | 2079410 A | * | 1/1982 | A61M 39/284 |

OTHER PUBLICATIONS

International Search Report and Written Opinion for Application No. PCT/US2022/051421, dated Mar. 17, 2023, 17 pages.

* cited by examiner

*Primary Examiner* — Chelsea E Stinson
*Assistant Examiner* — Eric A Lange
(74) *Attorney, Agent, or Firm* — MASCHOFF BRENNAN

(57) ABSTRACT

A universal flow limiter assembly includes a body configured to receive a portion of an IV tube, where the body includes two opposing side beams, a hinge portion disposed at a first end of the body, a control portion disposed at a second end of the body, a groove defined between the side beams and disposed between the hinge portion and the control portion and a control knob. The universal flow limiter assembly is configured to regulate a flow rate of fluid flowing through the IV tube based on rotation of the control knob. IV sets with universal flow limiter assemblies and methods of operating universal flow limiter assemblies are also provided.

9 Claims, 9 Drawing Sheets

300

310
Insert tubing into body of flow limiter assembly

320
Squeeze tubing into tubing clamp slot

330
Insert control knob into or onto body

340
Rotate control knob by hand or machine

350
Adjust control knob position to achieve desired tubing clamp slot deflection

| Gap Sizing - Potential Variant 1 | | | |
|---|---|---|---|
| | Small | Med | Large |
| | | | |
| Gap thickness | 0.027 | 0.036 | 0.050 |
| | | | |
| Tubing 2t max | 0.040 | 0.055 | 0.075 |
| Tubing 2t min | 0.030 | 0.040 | 0.055 |
| | | | |
| Compression max | -33% | -35% | -34% |
| Compression min | -10% | -10% | -10% |
| | | | |
| | | | |
| | | | |
| Gap Sizing - Potential Variant 2 | | | |
| | Small | Med | Large |
| | | | |
| Gap thickness | 0.015 | 0.020 | 0.030 |
| | | | |
| Tubing 2t max | 0.040 | 0.055 | 0.075 |
| Tubing 2t min | 0.030 | 0.040 | 0.055 |
| | | | |
| Compression max | -63% | -64% | -60% |
| Compression min | -50% | -50% | -45% |

FIG. 14

UNIVERSAL FLOW LIMITER ASSEMBLY

CROSS-REFERENCE TO RELATED APPLICATIONS

This application claims the benefit of priority under 35 U.S.C. § 119 to U.S. Provisional Patent Application Ser. No. 63/292,306, entitled "UNIVERSAL FLOW LIMITER ASSEMBLY," filed on Dec. 21, 2021, the entirety of which is incorporated herein by reference.

TECHNICAL FIELD

The present disclosure generally relates to a gravity intravenous (IV) set or infusion pump flow control device, and in particular a universal flow limiter assembly.

BACKGROUND

Flow controllers in the form of roller clamps or slide clamps are used in the medical field for intravenous (IV) applications. Typical roller clamps control a flow rate through an IV tube by clamping the tube in between a roller wheel and a linear housing having a relatively short length. This approach, however, typically requires that the housing and the roller wheel be sized for a particular size of IV tubing.

Also, typical roller clamps have flow rate drifting issues based on slippage of the roller wheel, such as when fluid pressure in the tube causes the roller wheel to roll back from the adjusted position. Further, typical roller clamps are manual devices that require a user, such as a health care clinician, to adjust the roller clamp by hand. In addition, typical roller clamps must be adjusted by manipulating the roller wheel all the way in one direction to provide a full clamping (e.g., no flow) state.

Further, typical slide clamps are sized for a specific size of IV tubing and only rough manual adjustments are possible by manually moving the IV tubing within the clamp between the smallest allowable tubing slot and one or more larger tubing slots and/or out of the clamping region entirely. Thus, the typical slide clamp provides only a few flow settings and does not interface with a machine for control.

Thus, it is desirable to provide a clamp assembly that provides a quick setting change to either full clamping with no flow or full open flow, while still providing a way to gradually release clamping pressure to achieve a target flow rate. It is also desirable to provide a clamp assembly that allows for use with multiple tubing sizes, provide both human and machine interfaces to enable manual and/or machine driven adjustments to the flow rate, and to eliminate or minimize flow rate slippage.

SUMMARY

In some embodiments of the disclosure, a universal flow limiter assembly comprises: a body configured to receive a portion of an intravenous (IV) tube, the body comprising: two opposing side beams; a hinge portion disposed at a first end of the body; a control portion disposed at a second end of the body; a groove defined between the side beams and disposed between the hinge portion and the control portion; and a control knob, wherein the universal flow limiter assembly is configured to regulate a flow rate of fluid flowing through the IV tube.

In some embodiments of the disclosure, an IV set comprises: an IV tube; an infusion component coupled to the IV tube; and a universal flow limiter assembly coupled to the IV tube, the universal flow limiter assembly comprising: a body configured to receive a portion of an IV tube, the body comprising: two opposing side beams; a hinge portion disposed at a first end of the body, the hinge portion configured to provide a biasing force on the opposing side beams towards each other; a control portion disposed at a second end of the body; a groove defined between the side beams and disposed between the hinge portion and the control portion; and a control knob comprising: a control body configured to couple with the control portion; a manual interface disposed on a first portion of the control body, the manual interface configured to be manipulated by hand to rotate the control knob; and a machine interface disposed on a second portion of the control body, the machine interface configured to be manipulated by a motor to rotate the control knob, wherein the universal flow limiter assembly is configured to regulate a flow rate of fluid flowing through the IV tube.

In some embodiments of the disclosure, a method of operating a universal flow limiter assembly comprises: inserting an IV tube laterally into a tube opening in the control portion at the second end of the body of a universal flow limiter assembly comprising: a body configured to receive a portion of an IV tube, the body comprising: two opposing side beams; a hinge portion disposed at a first end of the body; a control portion disposed at a second end of the body; a groove defined between the side beams and disposed between the hinge portion and the control portion; and a control knob; sliding the IV tube into a tubing clamp slot of the groove having a smallest width that the IV tube fits into without compression of a fluid flow path within the IV tube; coupling the control knob of the universal flow limiter assembly within a control receptacle of the control portion of the universal flow limiter assembly; rotating the control knob by one of: machine rotation by a motor, wherein the control knob is coupled to the motor; and manual rotation by hand; and adjusting, by rotation of the knob, a deflection between the side beams due to a biasing force of the hinge portion to one of expand and compress the IV tube to set a fluid flow rate through the IV tube to a determined rate.

In some embodiments of the disclosure, a method of operating a universal flow limiter assembly comprises: inserting an IV tube through an opening in the hinge portion of a universal flow limiter assembly comprising: a body configured to receive a portion of an IV tube, the body comprising: two opposing side beams; a hinge portion disposed at a first end of the body; a control portion disposed at a second end of the body; a groove defined between the side beams and disposed between the hinge portion and the control portion; and a control knob; sliding the IV tube into a tubing clamp slot of the groove having a smallest width that the IV tube fits into without compression of a fluid flow path within the IV tube; rotating the control knob by one of: machine rotation by a motor, wherein the control knob is coupled to the motor; and manual rotation by hand; and adjusting, by rotation of the knob, a deflection between clamp beams of the side beams due to force of a control portion of the control knob on guide surfaces of the clamp beams to one of expand and compress the IV tube to set a fluid flow rate through the IV tube to a determined rate.

The foregoing and other features, aspects and advantages of the disclosed embodiments will become more apparent from the following detailed description and accompanying drawings.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

FIG. 14 illustrates a chart for two different gap sizing examples, according to aspects of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
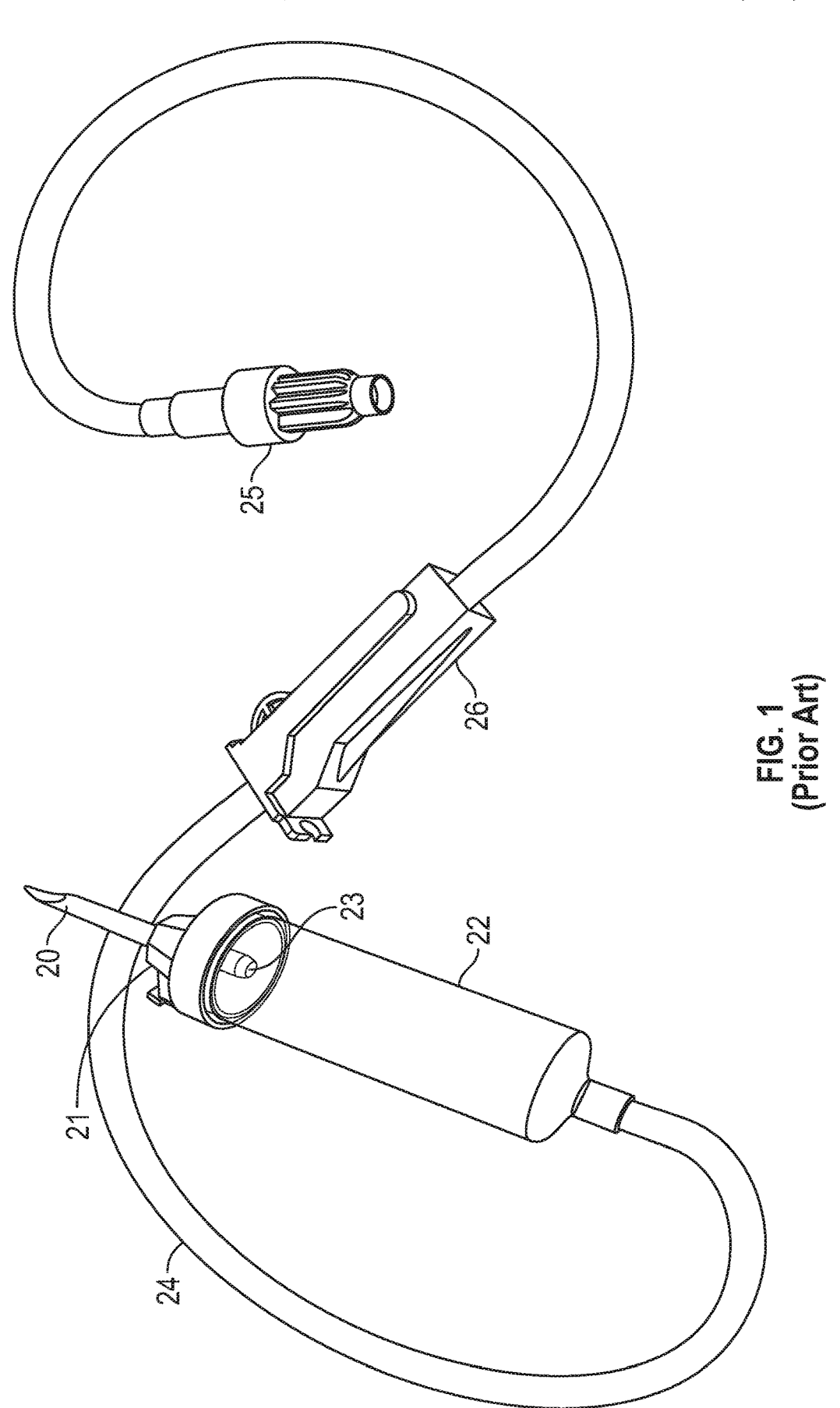
FIG. 1 depicts a perspective view of an example infusion set having a typical roller clamp.

The present disclosure relates to a roller clamp and in particular to a roller clamp for use in gravity infusion. The roller clamp regulates the flow rate of a medical fluid (for example a solution of a drug to be administered to a patient, or blood) flowing through a tube. Typically, a standard infusion set is used to infuse the fluid. An example of a standard infusion set is shown in FIG. 1.

The infusion set includes a piercing spike 20 which may either be a sharp spike for piercing rubber stoppers or rounded and blunt for insertion into a bag. The spike contains one channel for fluid and optionally a second channel for venting. A vent 21 is usually present in the vicinity of the piercing spike to allow air to flow into the drop chamber 22. The vent 21 may be provided with a bacterial filter to prevent bacteria from entering the equipment.

The drop chamber 22 has a drop generator 23 at the top of the drop chamber 22 that produces drops of a certain size. Drops from the drop generator 23 fall into the drop chamber 22 such that the drop chamber 22 is partially filled with liquid. This prevents air bubbles from entering the connector tube 24, which would be harmful to a patient. A particle filter may be provided at the lower aperture of the drop chamber 22.

The connector tube 24 connects the drop chamber 22 with the patient. The connector tube 24 is usually around 150 cm long and can be manufactured from PVC. The tube 24 is shown shortened in FIG. 1 for clarity. The connector tube 24 typically has a continuous diameter throughout the length of the tube.

At the end of the connector tube 24 is a Luer fitting 25 which is standardized for connection to all other pieces of apparatus having a standard Luer cone. The person skilled in the art will appreciate that the Luer fitting 25 can be fitted to a hypodermic needle (not shown) for infusing the medical fluid into the circulatory system of a patient (e.g., into a vein).

Between the drop chamber 22 and the Luer fitting 25 and engaging with the connector tube 24, is a roller clamp 26. The present disclosure is concerned with an improved roller clamp assembly, but a typical roller clamp 26 as known in the art will now be described for background information.

Figure 2:
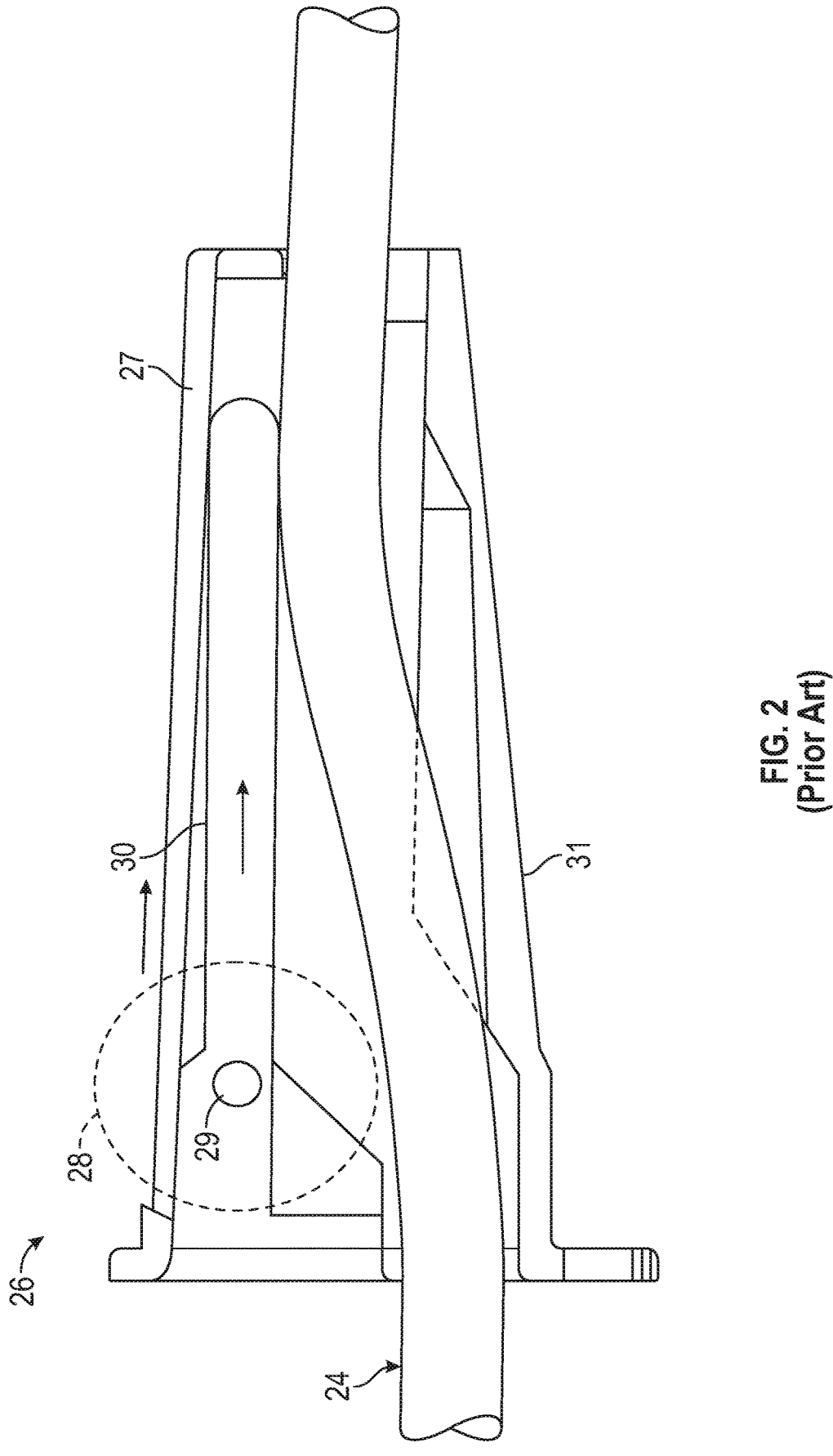
FIG. 2 depicts a cross-section side view of the roller clamp of FIG. 1.

The roller clamp 26 illustrated in FIG. 2 has two opposing side walls 27 having a pair of guide grooves 30 that are aligned with each other and face each other. A flow-regulating roller 28 is provided having axially-projecting shafts 29 protruding from the centers of each side of the roller 28. The roller 28 is shown in outline for clarity. The shafts 29 of the roller 28 are captured by and seated in the guide grooves 30 so that the roller 28 can move up and down the guide grooves 30 as indicated by the arrows in FIG. 2.

The entire roller clamp 26 has four walls (see FIG. 1) in an open-ended boxlike construction and is dimensioned and configured to receive the connector tube 24. In use, the tube 24 passes through the roller clamp 26, between the two opposing side walls 27, the roller 28 and a guide wall 31 that is opposed to the roller 28.

In the roller clamp 26, the surface of the guide wall 31 converges along its length toward the position of the guide grooves 30 in the downward direction of the guide grooves 30 (e.g., in the direction of the arrows in FIG. 2). This tends to urge the connector tube 24 within the roller clamp 26 toward the guide grooves 30 and thus toward roller 28.

Thus, rolling the roller 28 downwardly along the guide grooves 30 in the direction of the gradually closer guide wall 31 in the direction of the arrows causes the roller 28 to impinge against the connector tube 24. As the roller 28 impinges on the tube 24, the tube 24 becomes squeezed, as it is a flexible material such as PVC, and the lumen of the infusion tube 24 therefore becomes smaller. In this way, by narrowing of the lumen, the flow rate of liquid passing through the connector tube 24 can be regulated.

Thus, the roller clamp 26 controls the flow rate through the infusion tube 24 by clamping the infusion tube 24 between the roller 28 and the guide wall 31. As discussed above, this provides for a course flow rate change because a small movement of the roller 28 causes a large change in the flow rate of the fluid through the tube 24. Also, the force of the fluid in the tube 24 exerts a biasing force against the roller 28, which often leads to slippage of the roller 28 (e.g., the roller 28 rolls back) from the adjusted position. In addition, the roller clamp 26 requires manual adjustment and is not suitable for automated or processor controlled adjustment.

In aspects of the disclosure, universal flow limiter assemblies function as tubing clamps for IV tubing and IV sets. The universal flow limiter assembly provides full clamping (e.g., no flow) for a wide range of tubing sizes, provides the ability to manually and quickly release all of the clamping pressure to provide full open flow through the tubing, and provides the ability to gradually release the clamping pressure to provide for a target flow rate. The universal flow limiter assembly also provides for a human interface and a machine interface to the control element for the gradual clamping pressure release, thus providing for manual or machine driven adjustments to the target flow rate.

With reference to FIGS. 3-7, a universal flow limiter assembly 100 is shown. The universal flow limiter assembly 100 has a body 110 having a semi-rigid construction (e.g., hard plastic) and is dimensioned and configured to receive tubing, such as connector tube 24 (see FIG. 7). Two opposing side beams 112 define a groove 114 that consists of multiple tubing clamp slots 120. The groove 114 may be disposed between a hinge axis 116 and a control receptacle 118. For example, the opposing side beams 112 may join together at a hinge portion 115 in a U-shaped configuration, where the hinge axis 116 is an opening disposed within hinge portion 115. Thus, the hinge portion 115 may provide a biasing force that causes the opposing side beams 112 to be biased towards each other, thus providing a compressing or clamping force.

In addition, the control receptacle 118 may be disposed within a C-shaped control portion 117 of the body 110 having a tube opening 119 configured to have a tube 24 passed through the tube opening 119 and the control receptacle 118. The tube 24 may then be passed into the groove 114 and into the tubing clamp slot 120 with the smallest width that the tube 24 will fit into (see FIG. 7).

Figure 3:
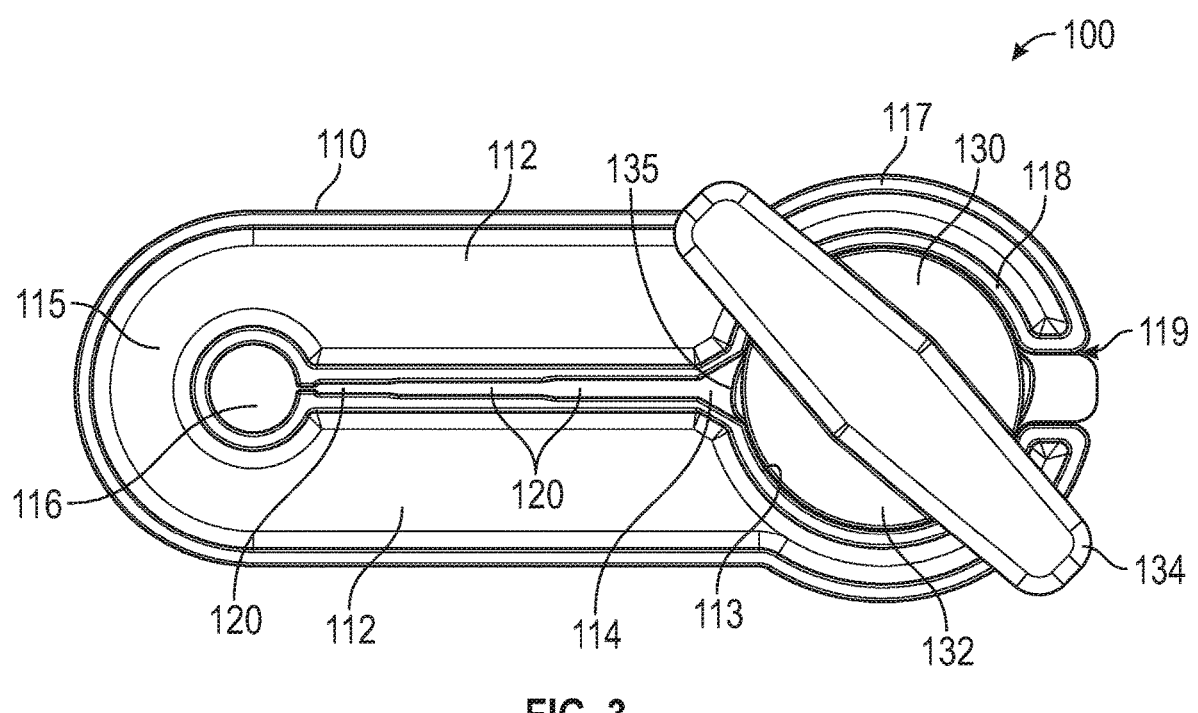
FIG. 3 depicts a front view of a universal flow limiter assembly in a fully clamped position, according to aspects of the disclosure.

A control knob 130 may include a body 132 sized and shaped to be disposed within the control receptacle 118. For example, the body 132 may be cylindrically shaped and sized to rotatingly fit within a circular shaped control receptacle 118. A manual interface 134 may be disposed on one end of the body 132, the manual interface 134 being configured to be grippable by a user's fingers. For example, as shown in FIG. 3, the manual interface 134 is a somewhat rectangular projection that protrudes outward from the body 110 so that it can be easily located, gripped and turned by hand.

Figure 4:
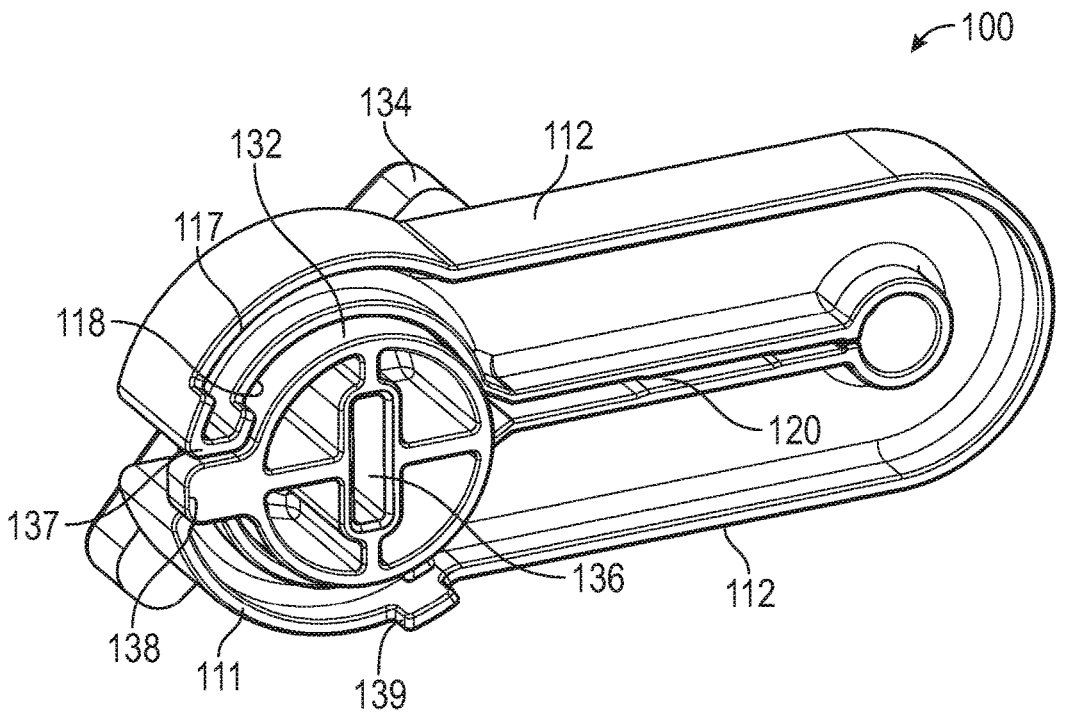
FIG. 4 depicts a perspective rear view of the universal flow limiter assembly of FIG. 3, according to aspects of the disclosure.
Figure 5:
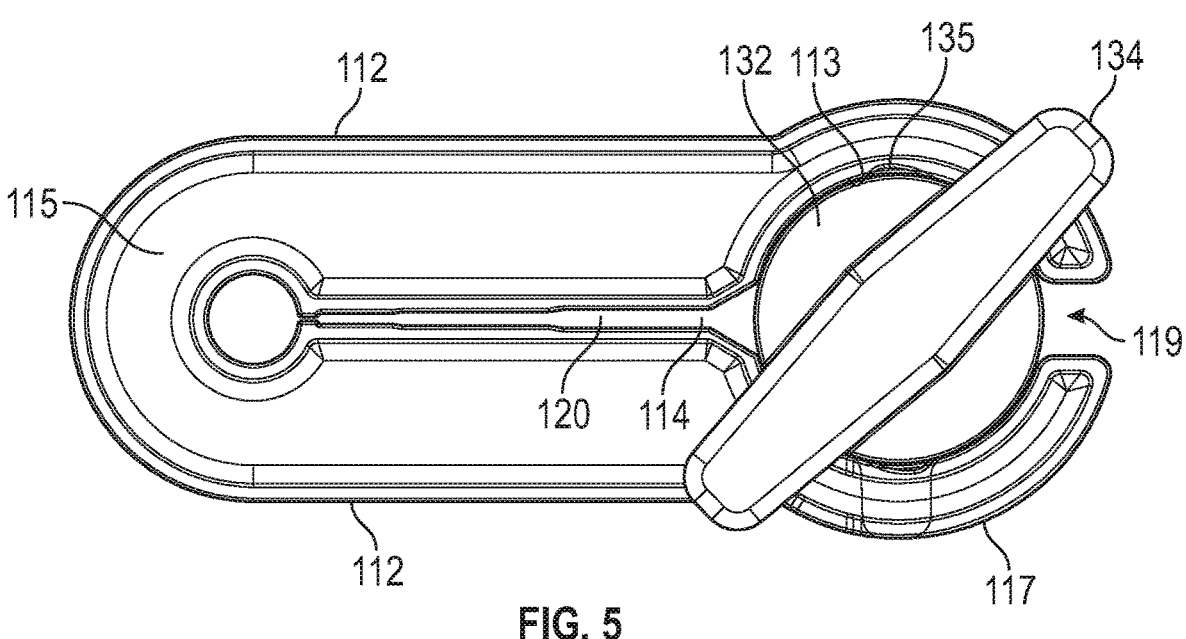
FIG. 5 depicts a front view of the universal flow limiter assembly of FIG. 3 in an adjusted flow rate position, according to aspects of the disclosure.

A machine interface 136 may be disposed at the opposing end of the body 132 from the manual interface 134. For example, as shown in FIG. 4, the machine interface 136 may be a slot-shaped channel disposed within a portion of the body 132, the machine interface 136 configured to receive a protrusion (e.g., slot-shaped protrusion) that is coupled to or part of a motor.

The control knob 130 may be formed of any suitable material, such as a combination of hard and soft plastic. For example, the body 132 and the machine interface 136 may be formed of hard plastic while the manual interface 134 may be formed of soft plastic to provide a more comfortable grip for a user's hand/fingers. As another example, the entire control knob 130 may be formed of hard plastic and the manual interface 134 may be overmolded with a softer material (e.g., rubber, soft plastic).

Figure 6:
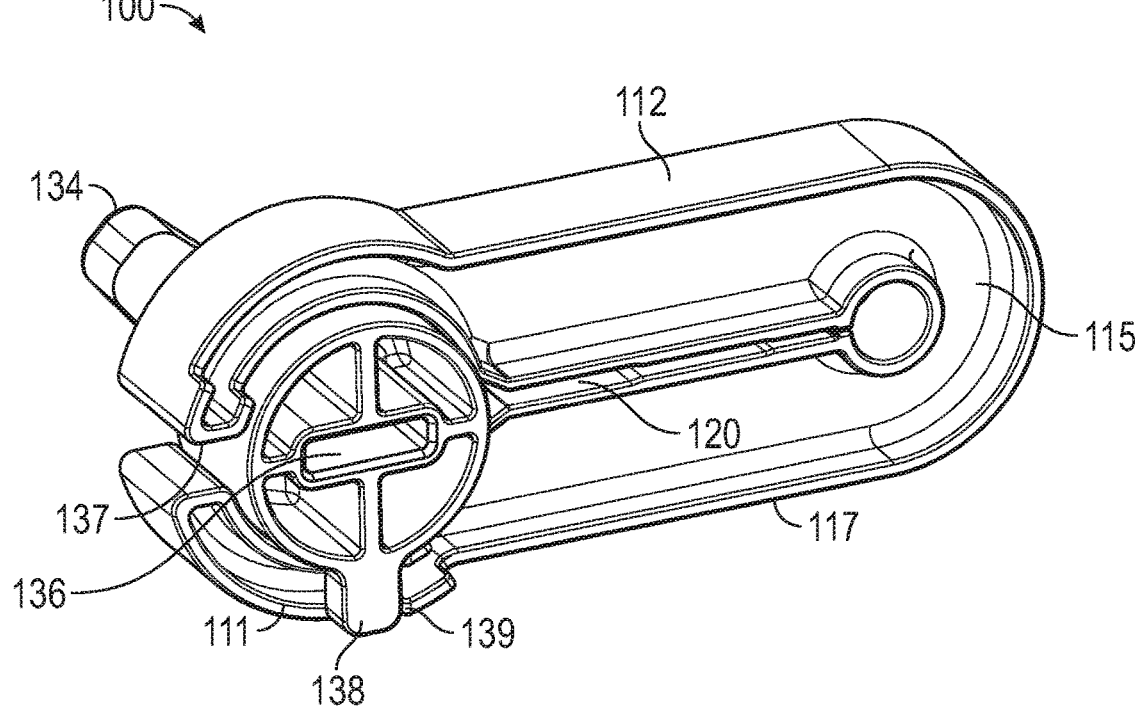
FIG. 6 depicts a perspective rear view of the universal flow limiter assembly of FIG. 4, according to aspects of the disclosure.
Figure 7:
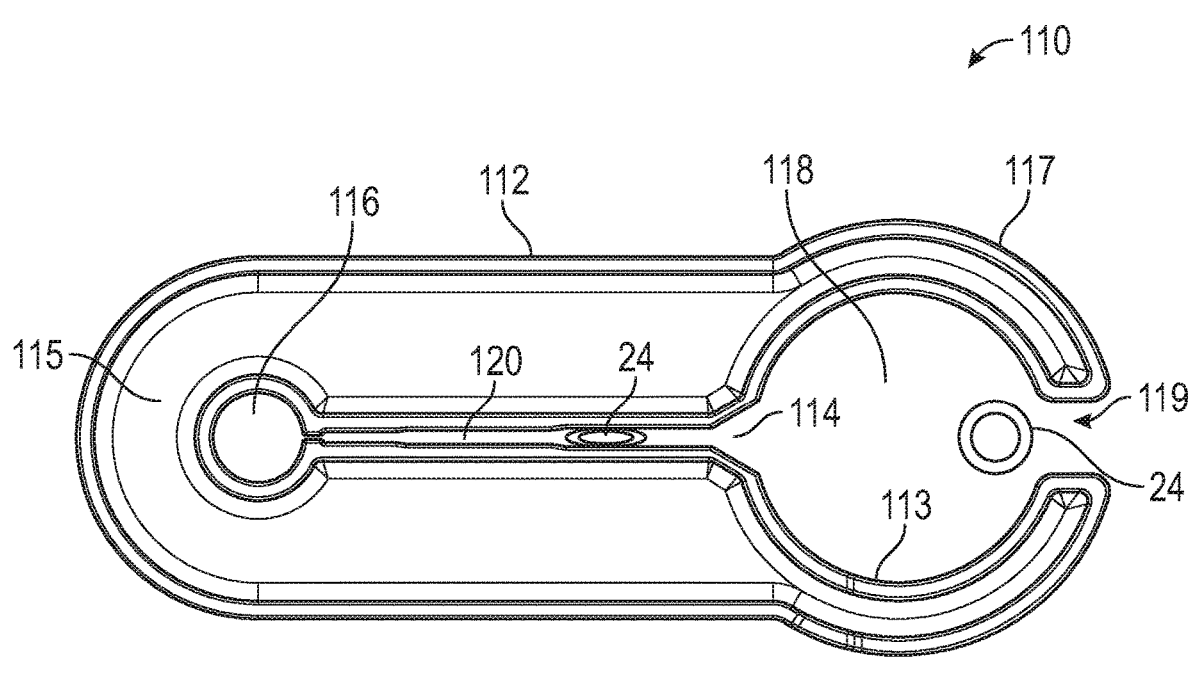
FIG. 7 depicts a front view of a universal flow limiter body assembly showing various IV tubing positions, according to aspects of the disclosure.
Figure 8:
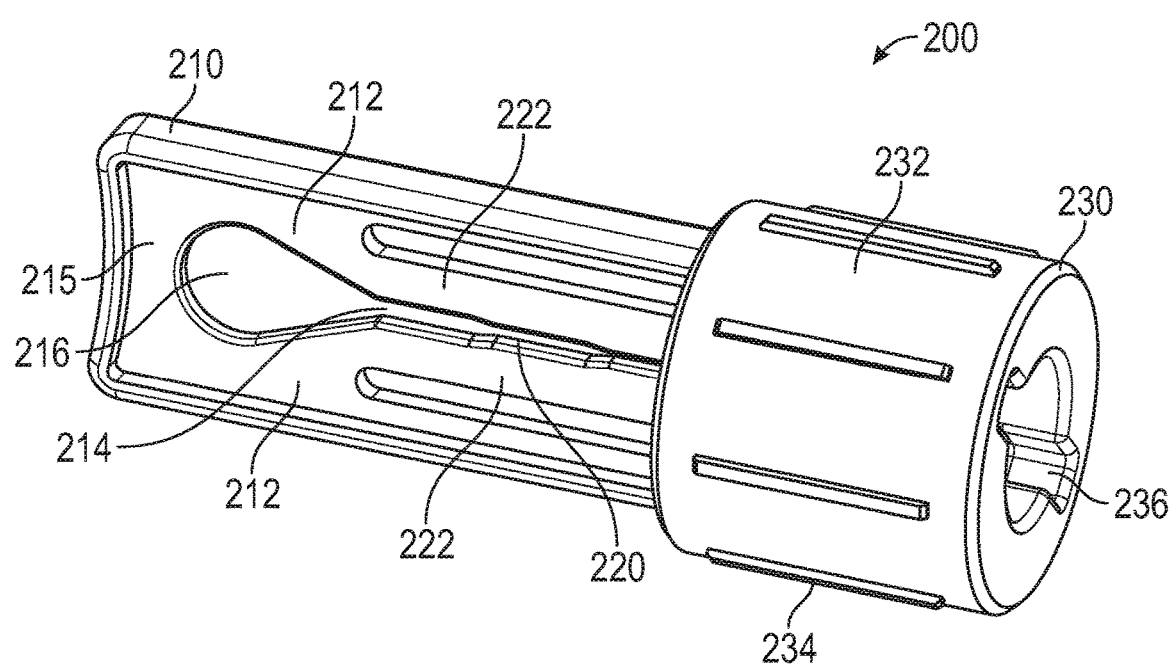
FIG. 8 depicts a perspective view of a universal flow limiter assembly, according to aspects of the disclosure.

A stop member 138 may protrude radially outward from the body 132. The stop member 138 may be configured to engage with a stop surface 137 disposed on one side beam 112 that forms part (e.g., one half) of the C-shaped control portion 117 when the control knob 130 is in the closed position (e.g., no flow setting), as shown in FIG. 4. The stop member 138 may also be configured to engage with a stop surface 139 disposed on the opposing side beam 112 that forms another part (e.g., the other half) of the C-shaped control portion 117 when the control knob 130 is in the open position (e.g., maximum flow setting), as shown in FIG. 6. The stop member 138 may be configured to slide or ride along a guide surface 111 of the side beam 112 that includes the stop surface 139. Thus, when the stop member 138 is at any position along the guide surface 111 between the two stop surfaces 137, 139, the flow rate will vary between shut off (e.g., no flow) and maximally open (e.g., maximum flow).

The control knob 130 may also include one or more cam surfaces 135 that extend radially outward from the body 132 and are configured to slidingly engage with an inner surface 113 of the control portion 117. For example, as the control knob 130 is turned, the cam surface(s) 135 interact with the inner surface 113 of the control portion 117, causing the C-shaped control portion 117 to pry apart. Here, the net effect of the prying open of the control portion 117 is to increase the width of the tubing clamp slots 120, thus allowing the tube 24 to expand (e.g., clamping pressure on tube is reduced) and resulting in greater fluid flow through the clamped portion of the tube 24. Here, the amount of deflection of the C-shaped control portion 117 is dependent upon the position of the cam surface 135 within the control receptacle 118, which provides for different flow rates to be selected.

In use, a body (e.g., body 110) of a universal flow limiter assembly (e.g., universal flow limiter assembly 100) is clamped over a tube (e.g., tube 24). Here, the tube is passed through an opening of the body (e.g., tube opening 119 and control receptacle 118), and then into a groove (e.g., groove 114) where the tube is squeezed into the smallest width of the groove (e.g., smallest width tubing clamp slot 120) that the tube will fit into. The control knob (e.g., control knob 130) is then inserted into the body (e.g., into the control receptacle 118).

As the control knob is turned (e.g., rotated within control receptacle 118), a cam (e.g., cam surface 135) interacts with an internal surface of the body (e.g., inner surface 113 of a control portion 117) to pry open a C-shape of the body (e.g., C-shaped control portion 117), which increases the width of the tubing clamp slot that is engaged with the tube. Thus, the clamping pressure on the tube is reduced and increased fluid flow may pass through the now semi-clamped tubing region. The flow rate may be adjusted to different flow rates by turning the control knob, thus changing the amount of deflection of the C-shaped area by the cam. In other words, the amount of deflection of the C-shape is dependent upon the position of the cam, which provides for different flow rates to be selected.

In aspects of the disclosure, universal flow limiter assembly 100 may provide a variety of benefits in comparison to typical tubing clamps. For example, universal flow limiter assembly 100 provides full clamping for a wide range of tubing sizes by having three discrete clamping regions to provide for target percentage compression ranges across a variety of tube thicknesses. In aspects of the disclosure, the universal flow limiter assembly 100 may include any suitable number of discrete clamping regions or tubing clamp slots 120 (e.g., 4 slots, 5 slots). Also, universal flow limiter assembly 100 provides a way to manually and quickly release all of the clamping pressure to allow full open flow through the tubing (e.g., tubing removed from clamping region).

In addition, universal flow limiter assembly 100 provides a way to gradually release the clamping pressure to allow a target flow rate to be achieved (e.g., control knob 130 with cam surfaces 135 interacting with the body 110). Further, universal flow limiter assembly 100 provides both human and machine interfaces such as a knob handle (e.g., manual interface 134) and a slot (e.g., machine interface 136). In aspects of the disclosure, the manual interface may be any suitable grasping feature (e.g., circular dial, single arm) and the machine interface may be any suitable motor coupling (e.g., toothed opening).

With reference to FIGS. 8-12, a universal flow limiter assembly 200 is shown. The universal flow limiter assembly 200 has a body 210 having a semi-rigid construction (e.g., hard plastic) and is dimensioned and configured to receive tubing, such as connector tube 24. Two opposing side beams 212 include clamp beams 222 that define a groove 214 consisting of multiple tubing clamp slots 220. The groove 214 may be disposed between a hinge axis 216 and a control region 218 (e.g., control portion). For example, the opposing side beams 212 may join together at a hinge portion 215 in a squared U-shaped configuration, where the hinge axis 216 is an opening disposed within the hinge portion 215. Thus, the hinge portion 215 may provide a biasing force that causes the opposing clamp beams 222 to be biased towards each other, thus providing a compressing or clamping force.

In aspects of the disclosure, the control region 218 may be configured as a control portion 217 of the body 210 having a tubing clamp slot 220 open to the end of the control region 218. A tube opening 219 is disposed at an opposing end of the body 210 from the control portion 217 and configured to have a tube 24 passed through the tube opening 219. In aspects of the disclosure, the tube 24 may be passed from the tube opening 219 into the groove 214 and into the tubing clamp slot 220 with the smallest width that the tube 24 will fit into, after which a control knob 230 may be coupled to the body 210. In aspects of the disclosure, the control knob 230 may already be coupled to the body 210 before the tube 24 is inserted. In aspects of the disclosure, the universal flow limiter assembly 200 may be provided with the tube 24 already installed, such as with a pre-assembled IV set, for example.

The control knob 230 may include a control body 232 sized and shaped to be coupled with the control portion 217. For example, the control body 232 may be cylindrically shaped and sized to rotatingly fit within and around a circular shaped control portion 217 (e.g., cylindrical outer wall). In aspects of the disclosure, the body 210 may include threads a disposed on the control portion 217 such that the control knob 230 is configured to rotatingly thread to the control portion 217 of the body 210.

Figures 9, 10:
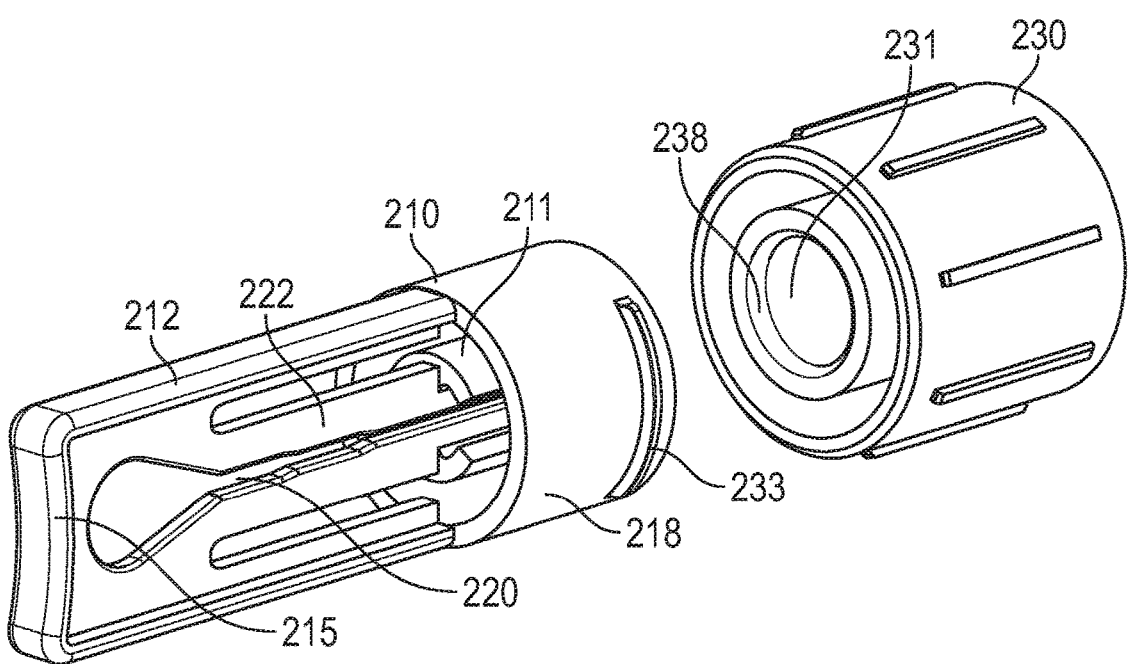
FIG. 9 depicts an exploded perspective view of the universal flow limiter assembly of FIG. 8, according to aspects of the disclosure.
FIG. 10 depicts another exploded perspective view of the universal flow limiter assembly of FIG. 8, according to aspects of the disclosure.

A manual interface 234 may be disposed radially around the control body 232, the manual interface 234 being configured to be grippable by a user's fingers. For example, as shown in FIG. 9, the manual interface 234 is multiple linear projections that protrude radially outward from the control body 232 so that the control knob 230 may be easily gripped and turned by hand. A machine interface 236 may be disposed at an end of the control body 232. For example, as shown in FIG. 9, the machine interface 236 may be a slot-shaped channel disposed within a portion of the control body 232, the machine interface 236 configured to receive a protrusion (e.g., slot-shaped protrusion) that is coupled to or part of a motor.

The control knob 230 may be formed of any suitable material, such as a combination of hard and soft plastic. For example, the control body 232 and the machine interface 236 may be formed of hard plastic while the manual interface 234 may be formed of soft plastic to provide a more comfortable grip for a user's hand/fingers. As another example, the entire control knob 230 may be formed of hard plastic and the manual interface 234 may be overmolded with a softer material (e.g., rubber, soft plastic).

Figures 11, 12:
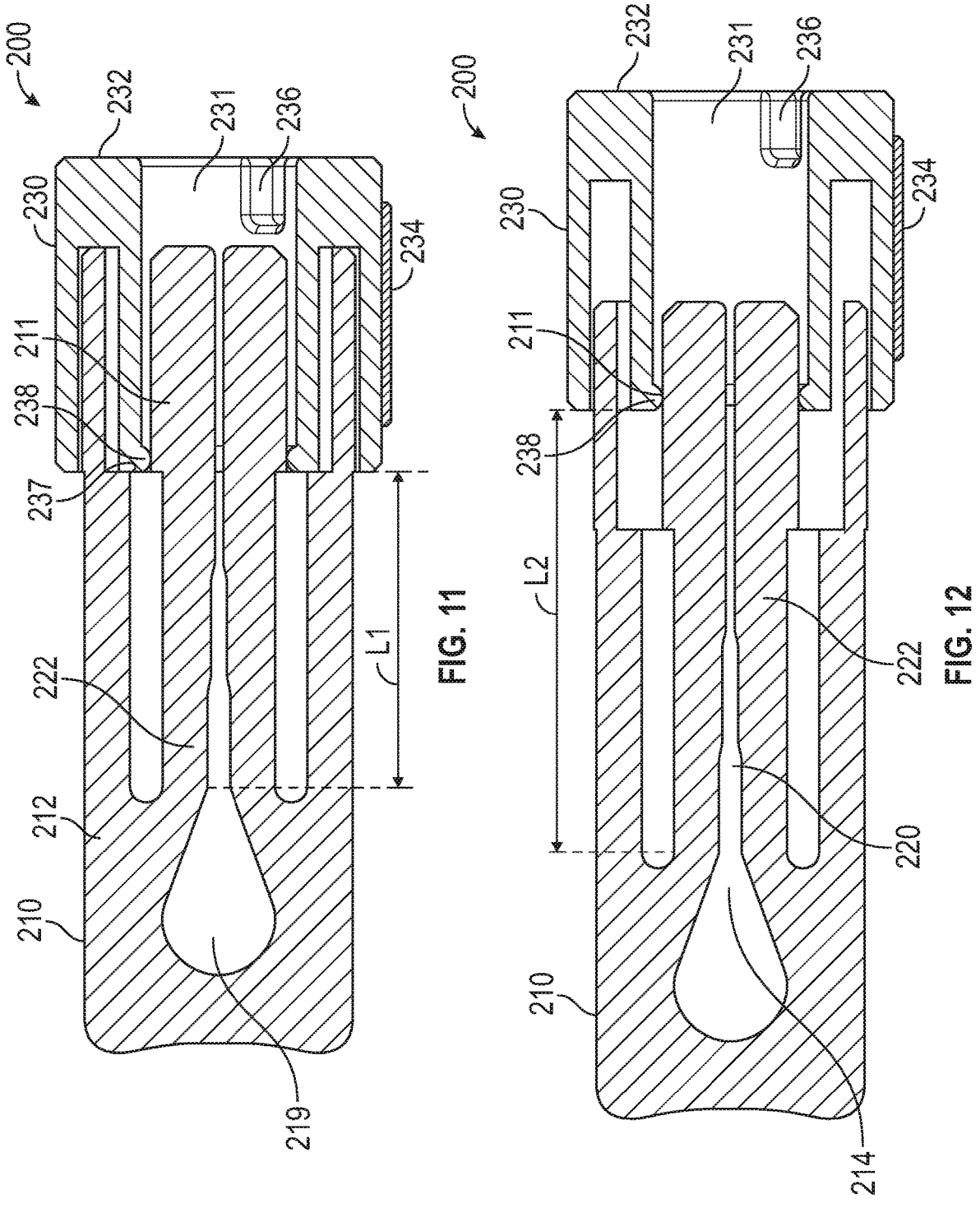
FIG. 11 depicts a cross-section front view of the universal flow limiter assembly of FIG. 8 in a closed position, according to aspects of the disclosure.
FIG. 12 depicts a cross-section front view of the universal flow limiter assembly of FIG. 8 in a reduced clamping force position, according to aspects of the disclosure.

A control member 238 may be disposed at an inner end of the control body 232 and may protrude radially inward into a central bore 231 of the control body 232. The control member 238 may be configured to engage with a stop surface 237 disposed on each side beam 212 when the control knob 230 is in the closed position (e.g., no flow setting), as shown in FIG. 11. The control member 238 may be configured to rotatingly slide or ride along guide surfaces 211 disposed radially around the clamp beams 222 when the control knob 230 is rotated out to the open position (e.g., maximum flow setting), as shown in FIG. 12. For example, each guide surface 211 may be an arc shaped surface disposed partially around the corresponding clamp beam 222. Thus, when the control member 238 is at any position along the guide surface 211 between the stop surfaces 237 and the fully open position on the clamp beams 222, the flow rate will vary between shut off (e.g., no flow) and maximally open (e.g., maximum flow).

In aspects of the disclosure, as the control knob 230 is rotated outward (e.g., unwound), a beam length (e.g., beam length L1 defined by the length of the clamp beams 222 axially inward of the control member 238 when the control knob 230 is in the closed position) is increased to a longer beam length (e.g., beam length L2 defined by the length of the clamp beams 222 axially inward of the control member 238 when the control knob 230 is in the open position), as shown in FIGS. 11 and 12. As the beam length increases from L1 to L2, the longer beam length allows for greater deflection of the clamp beams 222, which results in lower clamping pressure against the tube 24.

In use, a body (e.g., body 210) of a universal flow limiter assembly (e.g., universal flow limiter assembly 200) is clamped over a tube (e.g., tube 24). Here, the tube is passed through an opening of the body (e.g., tube opening 219), and then into a groove (e.g., groove 214) where the tube is squeezed into the smallest width of the groove (e.g., tubing clamp slot 220 with smallest width) that the tube will fit into. The control knob (e.g., control knob 230) is then inserted onto the body (e.g., onto the control region 218). In aspects of the disclosure, the above-described tube coupling process may be done to couple the universal flow limiter assembly to an IV tube of an IV set prior to placing the IV set into service, or the tube coupling process may be done with an IV tube that is already in use.

As the control knob is turned (e.g., rotated about the control region 218), a surface (e.g., control member 238) interacts with a surface of the body (e.g., guide surfaces 211 of the clamp beams 222) to rotatingly slide away from the hinge portion of the body (e.g., hinge portion 215), which increases the effective beam length (e.g., L1 to L2) and provides for greater beam deflection (e.g., increasing the width of the tubing clamp slot 220 that is engaged with the tube) under the load from the tubing. For example, the resiliency of the tubing and the fluid pressure in the tubing may force the tubing to expand out as far as the tubing clamp slot will allow. Thus, when the clamping pressure on the tube is reduced, an increased fluid flow may pass through the now semi-clamped tubing region (e.g., expanded inner diameter). The flow rate may be adjusted to different flow rates by turning the control knob, thus changing the beam length and the amount of deflection of the clamp beams. Here, small adjustments in the beam length may result in small adjustments in flow rate.

In aspects of the disclosure, universal flow limiter assembly 200 may provide a variety of benefits in comparison to typical tubing clamps. For example, universal flow limiter assembly 200 provides full clamping for a wide range of tubing sizes by having three discrete clamping regions to provide for target percentage compression ranges across a variety of tube thicknesses. In aspects of the disclosure, the universal flow limiter assembly 200 may include any suitable number of discrete clamping regions or tubing clamp slots 120 (e.g., 4 slots, 5 slots). Also, universal flow limiter assembly 200 provides a way to manually and quickly release all of the clamping pressure to allow full open flow through the tubing (e.g., tubing removed from clamping region).

In addition, universal flow limiter assembly 200 provides a way to gradually release the clamping pressure to allow a target flow rate to be achieved (e.g., control member 238 interacting with the guide surfaces 211 of the clamp beams 222). Further, universal flow limiter assembly 200 provides both human and machine interfaces such as a knob with multiple protrusions (e.g., manual interface 234) and a slot (e.g., machine interface 236). In aspects of the disclosure, the manual interface may be any suitable grasping feature (e.g., extending arms, textured outer surface) and the machine interface may be any suitable motor coupling (e.g., toothed opening).

Figure 13:
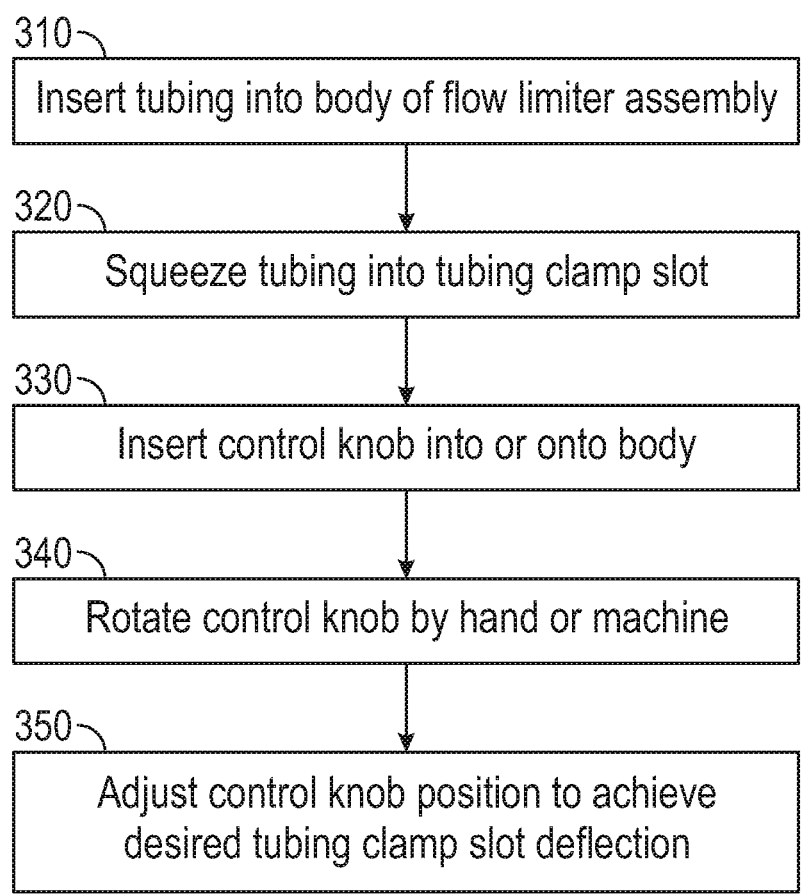
FIG. 13 illustrates a method of operating a universal flow limiter assembly, according to aspects of the disclosure.

With reference to FIG. 13, a method 300 of operating a universal flow limiter assembly (e.g., universal flow limiter assembly 100, 200) is provided. In step 310, tubing (e.g., IV tube 24) is placed or inserted into a body (e.g., body 110, 210) such that the tubing is disposed within a groove (e.g., groove 114, 214). The tubing is squeezed into a slot in the groove (e.g., tubing clamp slot 120, 220) having the smallest width that the tube can be fit into (e.g., without compressing a fluid flow path within the tube), in step 320.

In step 330, a control knob (e.g., control knob 130, 230) is inserted into/coupled onto the body (e.g., control receptacle 118, control region 218). The control knob is rotated by hand (e.g., by grasping and turning manual interface 134, 234) or by machine (e.g., by rotating motor element coupled to machine interface 136, 236) in step 340.

In step 350, the control knob is adjusted to the desired flow rate by rotating the control knob until the slot width deflects to expand or compress the tubing to achieve the desired flow rate. For example, regarding universal flow limiter assembly 100, as the control knob 130 is turned, the cam surface(s) 135 interact with the inner surface 113 of the control portion 117, causing the C-shaped control portion 117 to pry apart or to retract back under the biasing force of the hinge portion 115, depending upon which way the control knob 130 is turned. As another example, regarding universal flow limiter assembly 200, as the control knob 230 is turned, the control member 238 rotatingly slides or rides along guide surfaces 211 of the clamp beams 222, causing the clamp beams 222 to pry apart or to retract back under the biasing force of the hinge portion 215, depending upon which way the control knob 230 is turned.

Non-pressure rated tubing typically is made from similar wall thicknesses. In aspects of the disclosure, a universal flow limiter assembly (e.g., tubing clamp) may include three discrete zones of compression (e.g., gap size of tubing clamp slot). Thus, the universal flow limiter assembly may be configured to work with small, medium and large tubing diameters or thicknesses. For example, as shown in FIG. 14, a first gap sizing variation may include small, medium and large gap widths of 0.027, 0.036 and 0.050, respectively, while a second gap sizing variation may include small, medium and large gap widths of 0.015, 0.020 and 0.030, respectively. Thus, the gap sizing may be configured depending upon the desired percent of tube compression needed.

In one or more embodiments, a universal flow limiter assembly comprises: a body configured to receive a portion of an intravenous (IV) tube, the body comprising: two opposing side beams; a hinge portion disposed at a first end of the body; a control portion disposed at a second end of the body; a groove defined between the side beams and disposed between the hinge portion and the control portion; and a control knob, wherein the universal flow limiter assembly is configured to regulate a flow rate of fluid flowing through the IV tube.

In aspects of the disclosure, the hinge portion is a U-shaped joining of the opposing side beams. In aspects of the disclosure, the hinge portion comprises a hinge axis defined by an opening in the hinge portion, and wherein the hinge portion is configured to provide a biasing force on the opposing side beams towards each other. In aspects of the disclosure, the control portion comprises a C-shaped control portion defined by mirrored ends of the opposing side beams, and wherein a control receptacle is disposed within the C-shaped control portion.

In aspects of the disclosure, the control knob comprises: a control body configured to be disposed within the control receptacle; a manual interface disposed on a first end of the control body, the manual interface configured to be manipulated by hand to rotate the control knob; and a machine interface disposed on a second end of the control body, the machine interface configured to be manipulated by a motor to rotate the control knob. In aspects of the disclosure, the control knob comprises a stop member extending radially outward from the control body, the stop member configured to engage with a first stop surface of a first side beam when the control knob is in a closed position setting and to engage with a second stop surface of a second side beam when the control knob is in a fully open position setting. In aspects of the disclosure, the second side beam comprises a guide surface disposed between an end of the second side beam and the second stop surface, and wherein the stop member is configured to ride along the guide surface when the control knob is rotated.

In aspects of the disclosure, the second end of the body comprises a tube opening disposed between two end portions of the C-shaped control portion, wherein the tube opening is configured to slidably receive a portion of the IV tube. In aspects of the disclosure, the groove comprises a plurality of tubing clamp slots. In aspects of the disclosure, each of the plurality of tubing clamp slots defines a different groove width, and wherein a first tubing clamp slot with a widest groove width is disposed adjacent the control portion and a second tubing clamp slot with a narrowest groove width is disposed adjacent the hinge portion.

In aspects of the disclosure, the hinge portion is a squared U-shaped joining of the opposing side beams, wherein the hinge portion comprises a hinge axis defined by an opening in the hinge portion, and wherein the hinge portion is configured to provide a biasing force of the opposing side beams towards each other. In aspects of the disclosure, each side beam comprises: a clamp beam; and an arc shaped guide surface extending radially around a portion of an end of the clamp beam. In aspects of the disclosure, the control portion comprises: a cylindrical outer wall; and a tubing clamp slot disposed between the clamp beams and having an end opening disposed between the arc shaped guide sur- faces.

In aspects of the disclosure, the control knob comprises: a control body having a cylindrical shape configured to be removably coupled to the cylindrical outer wall of the control portion; a manual interface disposed radially around the control body, the manual interface configured to be manipulated by hand to rotate the control knob; and a machine interface disposed at an outer end of the control body, the machine interface configured to be manipulated by a motor to rotate the control knob. In aspects of the disclo- sure, the manual interface comprises a plurality of linear projections protruding radially outward from the control body, and wherein the machine interface comprises a slot- shaped channel configured to receive a slot-shaped exten- sion of the motor. In aspects of the disclosure, the control knob comprises a control member disposed at an inner end of the control body and extending radially inward into a central bore of the control body, the control member con- figured to engage with a stop surface disposed on each side beam when the control knob is in a closed position setting. In aspects of the disclosure, the control member is config- ured to rotatingly slide along the arc shaped guide surfaces when the control knob is rotated between the closed position setting and a fully open position setting.

In one or more embodiments, an IV set comprises: an IV tube; an infusion component coupled to the IV tube; and a universal flow limiter assembly coupled to the IV tube, the universal flow limiter assembly comprising: a body config- ured to receive a portion of an IV tube, the body comprising: two opposing side beams; a hinge portion disposed at a first end of the body, the hinge portion configured to provide a biasing force on the opposing side beams towards each other; a control portion disposed at a second end of the body; a groove defined between the side beams and disposed between the hinge portion and the control portion; and a control knob comprising: a control body configured to couple with the control portion; a manual interface disposed on a first portion of the control body, the manual interface configured to be manipulated by hand to rotate the control knob; and a machine interface disposed on a second portion of the control body, the machine interface configured to be manipulated by a motor to rotate the control knob, wherein the universal flow limiter assembly is configured to regulate a flow rate of fluid flowing through the IV tube.

In one or more embodiments, a method of operating a universal flow limiter assembly comprises: inserting an IV tube laterally into a tube opening in the control portion at the second end of the body of a universal flow limiter assembly comprising: a body configured to receive a portion of an IV tube, the body comprising: two opposing side beams; a hinge portion disposed at a first end of the body; a control portion disposed at a second end of the body; a groove defined between the side beams and disposed between the hinge portion and the control portion; and a control knob; sliding the IV tube into a tubing clamp slot of the groove having a smallest width that the IV tube fits into without compression of a fluid flow path within the IV tube; coupling the control knob of the universal flow limiter assembly within a control receptacle of the control portion of the universal flow limiter assembly; rotating the control knob by one of: machine rotation by a motor, wherein the control knob is coupled to the motor; and manual rotation by hand; and adjusting, by rotation of the knob, a deflection between the side beams due to a biasing force of the hinge portion to one of expand and compress the IV tube to set a fluid flow rate through the IV tube to a determined rate.

In one or more embodiments, a method of operating a universal flow limiter assembly comprises: inserting an IV tube through an opening in the hinge portion of a universal flow limiter assembly comprising: a body configured to receive a portion of an IV tube, the body comprising: two opposing side beams; a hinge portion disposed at a first end of the body; a control portion disposed at a second end of the body; a groove defined between the side beams and disposed between the hinge portion and the control portion; and a control knob; sliding the IV tube into a tubing clamp slot of the groove having a smallest width that the IV tube fits into without compression of a fluid flow path within the IV tube; rotating the control knob by one of: machine rotation by a motor, wherein the control knob is coupled to the motor; and manual rotation by hand; and adjusting, by rotation of the knob, a deflection between clamp beams of the side beams due to force of a control portion of the control knob on guide surfaces of the clamp beams to one of expand and compress the IV tube to set a fluid flow rate through the IV tube to a determined rate.

It is understood that any specific order or hierarchy of blocks in the methods of processes disclosed is an illustra- tion of example approaches. Based upon design or imple- mentation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A universal flow limiter assembly comprising:
a body configured to receive a portion of an intravenous (IV) tube, the body comprising:
two opposing side beams;
a hinge portion disposed at a first end of the body;
a control portion disposed at a second end of the body, wherein the control portion comprises a C-shaped control portion defined by mirrored ends of the opposing side beams, and wherein a control receptacle is disposed within the C-shaped control portion; and
a groove defined between the side beams and disposed between the hinge portion and the control portion; and
a control knob, comprising:
a control body configured to be disposed within the control receptacle;
a manual interface disposed on a first end of the control body, the manual interface configured to be manipulated by hand to rotate the control knob; and
a machine interface disposed on a second end of the control body, the machine interface configured to be manipulated by a motor to rotate the control knob, wherein the control knob comprises a stop member extending radially outward from the control body, the stop member configured to engage with a first stop surface of a first side beam when the control knob is in a closed position setting and to engage with a second stop surface of a second side beam when the control knob is in a fully open position setting,
wherein the universal flow limiter assembly is configured to regulate a flow rate of fluid flowing through the IV tube.

2. The universal flow limiter assembly of claim 1, wherein the hinge portion is a U-shaped joining of the opposing side beams.

3. The universal flow limiter assembly of claim 2, wherein the hinge portion comprises a hinge axis defined by an opening in the hinge portion, and wherein the hinge portion is configured to provide a biasing force on the opposing side beams towards each other.

4. The universal flow limiter assembly of claim 1, wherein the second side beam comprises a guide surface disposed between an end of the second side beam and the second stop surface, and wherein the stop member is configured to ride along the guide surface when the control knob is rotated.

5. The universal flow limiter assembly of claim 1, wherein the second end of the body comprises a tube opening disposed between two end portions of the C-shaped control portion, wherein the tube opening is configured to slidably receive a portion of the IV tube.

6. The universal flow limiter assembly of claim 1, wherein the groove comprises a plurality of tubing clamp slots.

7. The universal flow limiter assembly of claim 6, wherein each of the plurality of tubing clamp slots defines a different groove width, and wherein a first tubing clamp slot with a widest groove width is disposed adjacent the control portion and a second tubing clamp slot with a narrowest groove width is disposed adjacent the hinge portion.

8. An intravenous (IV) set comprising:

an IV tube;

an infusion component coupled to the IV tube; and the universal flow limiter assembly of claim 1.

9. A method of operating a universal flow limiter assembly, the method comprising:

inserting an IV tube laterally into a tube opening in the control portion at the second end of the body of the universal flow limiter assembly of claim 1;

sliding the IV tube into a tubing clamp slot of the groove having a smallest width that the IV tube fits into without compression of a fluid flow path within the IV tube;

coupling the control knob of the universal flow limiter assembly within a control receptacle of the control portion of the universal flow limiter assembly;

rotating the control knob by one of:

machine rotation by a motor, wherein the control knob is coupled to the motor; and manual rotation by hand; and adjusting, by rotation of the knob, a deflection between the side beams due to a biasing force of the hinge portion to one of expand and compress the IV tube to set a fluid flow rate through the IV tube to a determined rate.

\* \* \* \* \*